(12) United States Patent
Marshall et al.

(10) Patent No.: US 8,486,007 B2
(45) Date of Patent: *Jul. 16, 2013

(54) INJECTION DEVICE

(75) Inventors: Jeremy Marshall, Oxford (GB); Steven Mark Guy Rolfe, Oxon (GB)

(73) Assignee: Owen Mumford Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/434,340

(22) Filed: Mar. 29, 2012

(65) Prior Publication Data

US 2012/0184900 A1 Jul. 19, 2012

Related U.S. Application Data

(63) Continuation of application No. 12/300,174, filed as application No. PCT/GB2007/001721 on May 11, 2007, now Pat. No. 8,167,834.

(30) Foreign Application Priority Data

May 11, 2006 (GB) .................................. 0609311.6

(51) Int. Cl.
*A61M 37/00* (2006.01)
*A61M 5/00* (2006.01)
*A61M 5/315* (2006.01)

(52) U.S. Cl.
USPC ............. 604/89; 604/191; 604/209; 604/211; 604/218

(58) Field of Classification Search
USPC ............... 604/82, 89, 90, 187, 191, 207–211, 604/218, 220, 224, 228
See application file for complete search history.

(56) References Cited

U.S. PATENT DOCUMENTS

| 5,971,953 | A | 10/1999 | Bachynsky |
| 6,319,225 | B1 | 11/2001 | Sugita et al. |
| 6,419,656 | B1 | 7/2002 | Vetter et al. |
| 6,645,179 | B1 | 11/2003 | Ishikawa et al. |
| 2006/0111666 | A1 | 5/2006 | Hommann et al. |
| 2006/0178641 | A1 | 8/2006 | Reynolds |
| 2008/0171969 | A1* | 7/2008 | Byrne et al. .................... 604/73 |
| 2008/0275387 | A1* | 11/2008 | Yeadon et al. .................. 604/82 |

FOREIGN PATENT DOCUMENTS

| EP | 0 338 806 | 10/1989 |
| EP | 1 066 847 | 1/2001 |
| EP | 1 759 728 | 3/2007 |
| EP | 1 038 543 | 9/2007 |
| JP | 2006068531 | 3/2006 |

OTHER PUBLICATIONS

Japanese Office Action, dated Jan. 24, 2012, in Application No. 2009-508492.

* cited by examiner

*Primary Examiner* — Victoria P Shumate
(74) *Attorney, Agent, or Firm* — Young & Thompson

(57) ABSTRACT

A pen injection device designed for use with dual or multi-chamber cartridges 14, is provided with an extended length plunger 24 having a non-drive portion 24' on its forward end and the usual screw-threaded drive portion 24" on its rearward end. This arrangement allows the plunger to be pushed forwardly while the dosing drive mechanism is disengaged to effect a reconstitution movement of the rearward bung 18' in the cartridge. Thereafter the threaded portion on the plunger 24' engages the drive mechanism to allow metered dosing.

20 Claims, 3 Drawing Sheets

INJECTION DEVICE

CROSS REFERENCE TO RELATED APPLICATIONS

This application is a continuation of application Ser. No. 12/300,174 filed on Dec. 9, 2008 and issued as U.S. Pat. No. 8,167,834 on May 1, 2012; which is the 35 U.S.C. 371 national stage of International application PCT/GB07/01721 filed on May 10, 2007; which claims priority to British application 0609311.6 filed on May 11, 2006. The entire contents of each of the above-identified applications are hereby incorporated by reference.

BACKGROUND OF THE INVENTION

This invention relates to an injection device and in particular, but not exclusively, to an injection device for use with dual or multi-chamber cartridges.

DESCRIPTION OF THE RELATED ART

In typical dual chamber cartridges two spaced bungs are disposed within the cartridge to define two separate chambers, for example a forward chamber containing lyophilised powder and a rearward chamber containing diluent liquid. A bypass channel in the cartridge wall provides a bypass path between the two chambers, but is initially closed by the presence of the forward bung. In use, as pressure is applied to the rearward bung to move it, the liquid in the diluent chamber and the forward bung move together forwardly and in doing so uncover the bypass channel so that the fluid from the diluent chamber flows into the forward chamber to mix with the lyophilised powder. The forward bung and the rearward bung may be of similar form or the forward item may be in the form of a moveable wall.

In such cartridges, it will be appreciated that two phases of movement of the rearward bung are required, namely a first, reconstitution phase during which the rearward bung moves to move the liquid in the rearward chamber forward to mix with the material in the forward chamber, and a second, dosing phase during which metered movement of the rearward bung is required to expel a preset dose.

In a typical pen injector such as our Autopen® device, the pen injector comprises a main body housing the pen injector mechanism which screws into a cartridge holder which holds the cartridge of therapeutic substance. In use the user dials in a required number of units dosage on a dose selector on the body and then presses the release button which causes an internal plunger in the body in contact with the bung to advance it by the required amount to expel a corresponding dose from the cartridge in the cartridge holder.

A problem arises in relation to such devices in relation to use with dual chamber cartridges because the amount of movement required during the reconstitution phase 15-20 mm or more is much greater than that required for the doses (typically 0.1 to 0.2 mm per unit dose). If the pen injector mechanism were to be used to try and achieve the length of stroke required for the reconstitution phase this would be extremely tedious requiring many cycles of repetitive dialing in and firing. A previous attempt to overcome this problem provided an pen injector in which the body and the cartridge holder had extended threaded mating sections so that the holder could be engaged with the body and screwed continuously until the plunger had driven the rearward bung by an amount sufficient for the reconstitution phase. Thereafter the pen injector mechanism could be operated as required to effect a series of doses. This extended screw thread arrangement is also extremely tedious and time consuming.

There is therefore a need for an injection device for use with a multi-chamber cartridge, to allow convenient reconstitution followed by the usual dose metering in successive injections.

BRIEF SUMMARY OF THE INVENTION

Accordingly, this invention provides an injection device for dispensing in use a substance from a dual or multi-chamber cartridge, said cartridge having a bung moveable in a first, reconstitution, extent of movement and a second, dosing, extent of movement (which may be variable), said device comprising:
 a body portion;
 a plunger mounted in said body portion for longitudinal movement with respect thereto in a forward dispensing direction to co-operate in use with said bung;
 a plunger drive element disposed adjacent said plunger for driving said plunger;
 said plunger having a drive portion adapted to mate with a complementary drive portion on said plunger drive element and adapted to impart dosing movement to said plunger;
 said drive portion extending only partly along said plunger to leave a forward non-drive portion;
 whereby, during a reconstitution phase, said plunger may be moved longitudinally forwards from a position with the non-drive portion adjacent said plunger drive element, to bring its drive portion into driving engagement with the drive portion on said plunger drive element.

In this manner, the plunger may be moved to effect reconstitution of the therapeutic mixture in the cartridge before the drive portions are engaged. This allows a separate reconstitution movement followed by a metered dosing movement of the plunger, without compromising the requirements of either movement.

Preferably, said drive portions on said drive element and said plunger are complementary threaded drive portions. Thus the plunger may carry a male thread and the drive element may include a bore having a female thread therein although the reverse is not excluded. In this instance, the non-drive portion of said plunger may comprise a non-threaded portion sized to be moveable freely through the drive element until the drive portions engage.

The initial reconstitution movement of the plunger may be achieved in various ways. In one arrangement a mover element is slideably moveable in said body portion and has an externally accessible push region so that the element may be manually pushed to engage said plunger and to move it longitudinally until said complementary drive portions are in driving engagement. The device preferably includes means for releasably preventing longitudinal movement of said mover element. This may typically comprise a bayonet type lock arrangement between the mover element and an element fixed with respect to the body portion. In addition, or alternatively, it may comprise a releasable spacer element.

Conveniently, the mover element includes a cap element defining the push region, said cap element being adapted to engage in snap engagement in an end region of said injection device.

Preferably, the device includes bias means for urging the plunger element towards complementary driving engagement with said drive element. Said bias means and said plunger are preferably arranged such that said plunger is isolated from the influence of the bias means a preset distance after initial driving engagement between said complementary drive portions.

The drive to the drive element may be achieved in various ways and in one embodiment, it is in the form of a drive mechanism which applies a pre-selectable amount of angular movement to said drive element on activation thereof. Thus the drive mechanism may comprise a user settable dose setting member rotatably mounted on said body portion to set a dose, with a spring acting between the dose setting member and the body portion, said spring being strained to a variable extent depending on movement of said dose setting member. A ratchet arrangement may be disposed between the dose setting member and said drive element, allowing one way relative movement therebetween as the dose setting member is rotated to set a dose. A trigger member may be provided to prevent rotary movement of the drive element during the dose setting routine but to be releasable thereafter to allow said spring to rotate said dose setting member and said drive element in unison by an amount corresponding to the set dose. In this arrangement, the dose setting element preferably includes a generally cylindrical portion surrounding at least part of the plunger.

The dose setting element may conveniently comprise a rotatable collar or the like on the rearward end of the injection device and, where provided, the mover element may be arranged to snap fit into said collar when the mover element is moved fully forward.

Whilst the invention has been described above, it extends to any inventive combination of the features set out above or in the following description.

BRIEF DESCRIPTION OF VIEWS OF THE DRAWINGS

The invention may be formed in various ways, and an embodiment thereof will now be described by way of example only, reference being made to the accompanying drawings in which.

DETAILED DESCRIPTION OF THE INVENTION

Figure 1A:
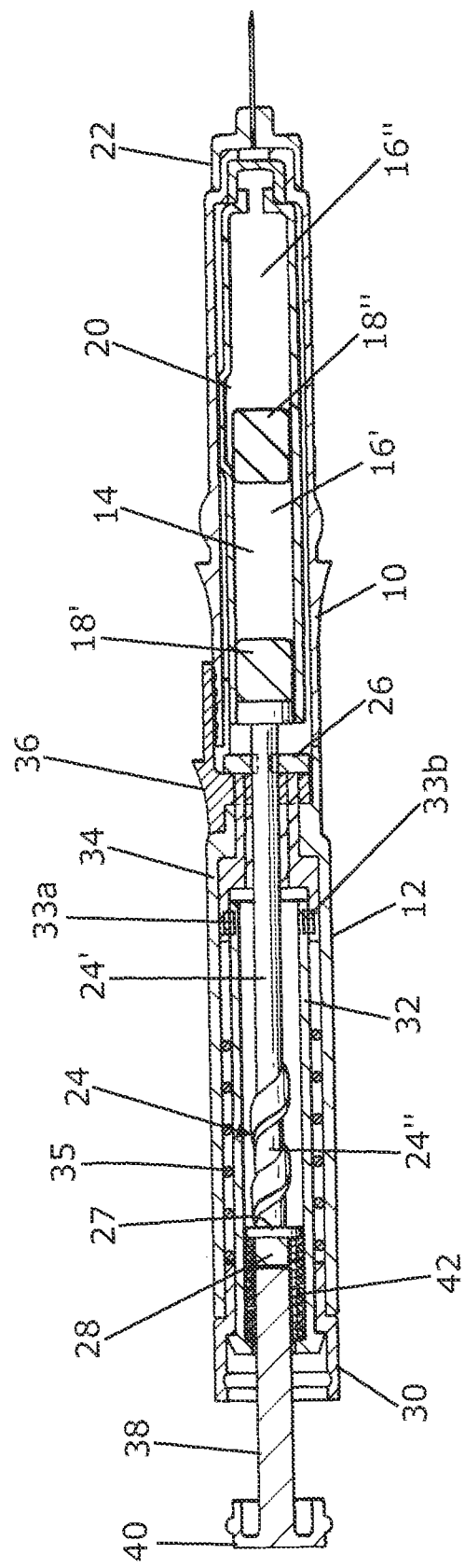
FIG. 1a is a schematic view of a pen injection device in accordance with this invention for use with a multi-chamber cartridge, before reconstitution.

In the drawings, a pen injection device is made up of a cartridge holder 10 screw-threaded onto a main body portion 12. Within the cartridge holder 10 is provided a dual chamber cartridge 14 having two chambers 16' and 16" defined by rearward and forward bungs 18', 18". The rearward chamber 16' normally contains a diluent liquid and the forward chamber 16" normally contains a lyophilised powder. Part way along the syringe, and initially closed off by the forward bung 18", is a bypass 20 channel disposed in the wall of the cartridge and interconnecting the forward and rearward chambers 16', 16". Screwed onto the end of the cartridge holder 10 is a double ended needle 22 which pierces a rubber membrane (not shown) in the front of the cartridge.

Figure 1B:
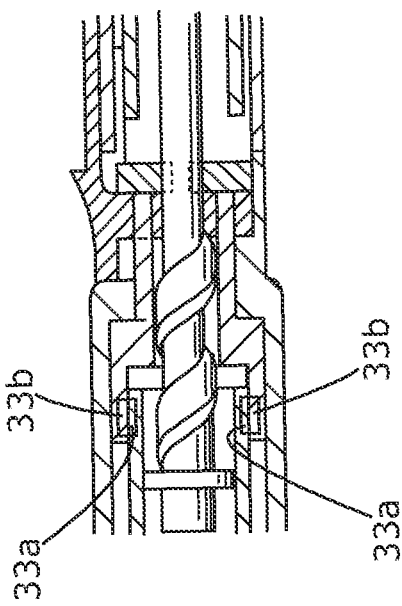
FIG. 1b is an expanded view of the ratchet mechanism.

The rearward bung 18' in use is acted upon and driven by a plunger 24. The plunger 24 can move linearly under certain conditions but is prevented from rotation by means of two diametrically opposed channels (not shown) which cooperate with a correspondingly shaped washer 26 itself held against rotation on the forward end of the main body portion 12. Unlike previous such devices, in which the plunger shaft has been threaded along its operational length, in this embodiment of the invention the forward two-thirds or so 24' of the plunger 24 is plain, but to the rear of this is a threaded section 24" which terminates in a flange 27 and a plain end 28. Rotatably fitted in the rearward end of the body portion 12 is a dose setting collar 30 which is fixedly connected to a setting cylinder 32 the forward end of which is provided with an externally directed ratchet surface 33a which cooperates with an internally directed ratchet surface 33b on the drive gear 34, as shown in FIG. 1b. The ratchet mechanism allows relative ratcheting movement of the dose setting collar 30 and the setting cylinder 32 relative to the drive gear 34 in a dose setting direction but not in the reverse, dose expelling direction. As drawn, the dose setting direction is clockwise when viewed on the rearward end of the device. A torsion spring 35 is secured at its rearward end to the dose setting collar and at its forward end is anchored to be rotationally fixed with respect to the main body 12. A trigger 36 is slidably mounted in said main body portion 12 and moveable against a spring bias from a forward position in which it locks the drive gear 34 against rotation and a rearward position in which the drive gear 34 is free to rotate.

In use of the metered dose setting drive mechanism, the required dose is dialed in by rotating the dose setting collar 30 by the required number of clicks provided by the ratchet between the setting cylinder 32 and the drive gear 34. During this setting routine, the drive sleeve 34 does not rotate, being kept still by the trigger 36 with the ratchet between the sleeve 32 and the drive gear 34 allowing relative movement between the two. Once the required number of clicks has been dialed in, the user then inserts the needle into the injection site and pushes the trigger 36 rearwardly to release the drive gear 34. The drive gear 34, now being free to rotate with the setting cylinder 32 and the setting collar 30, is driven by the torsion spring anticlockwise by an amount equivalent to the angular amount dialed into the dose setting collar 30. This rotary movement causes the plunger 24 to advance by virtue of its threaded engagement with the inside of the drive collar 34. Further details of suitable arrangements are described in our U.S. Pat. No. 5,104,380.

Figure 2:
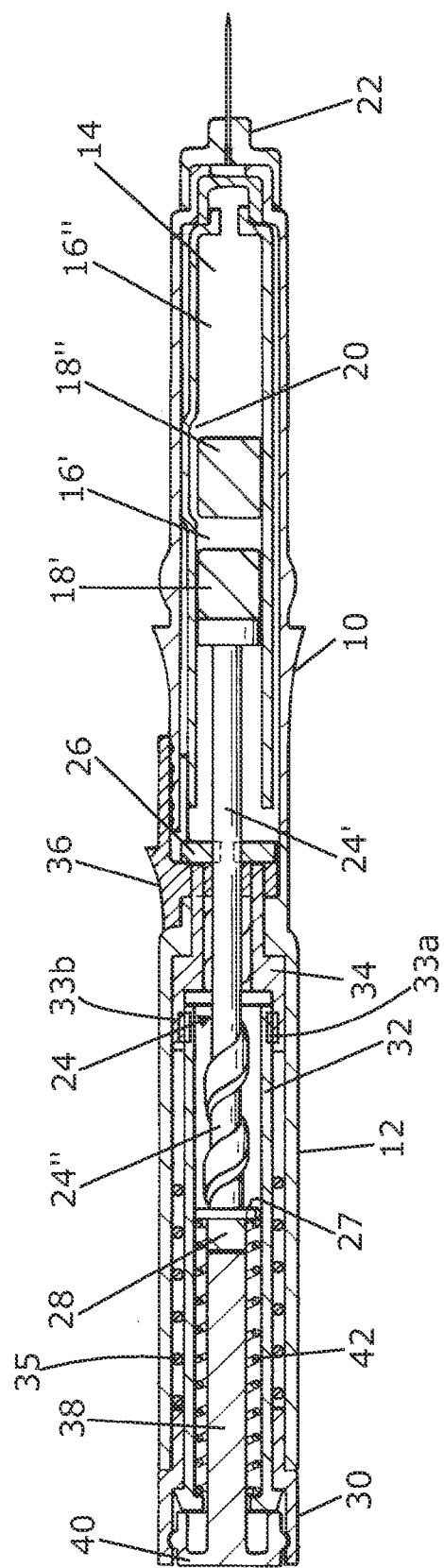
FIG. 2 is a schematic view similar to FIG. 1 but during the latter stages of reconstitution and before a dose has been set.
Figure 3:
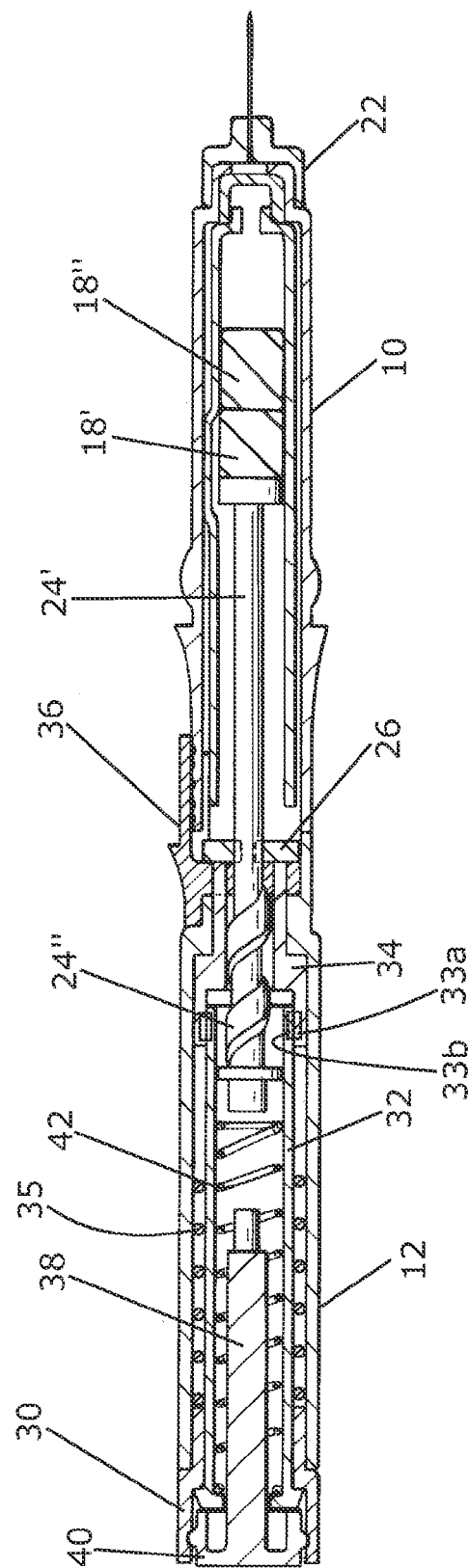
FIG. 3 is a schematic side view after a number of doses have been expelled.

As noted, in the embodiment of this invention, the plunger is threaded along only part of its length, the remainder being plain. The construction and operation of this device will now be described. In FIG. 1a, the plunger 24 is shown in its retracted position prior to driving the rearward bung 18' forwards. Slideably mounted in the end of the setting cylinder 32 is a pushrod 38 with a cap 40. The pushrod 38 is designed to be a sliding fit within the setting cylinder 32. Releasing the pushrod 38 and pushing it causes it to engage the plain end 28 of the plunger 24 so that the plunger can be moved longitudinally in a reconstitution phase from the position shown in FIG. 1a to that in FIG. 2. Once fully pressed in, the cap 40 on the pushrod 38 may snap-fit into the interior of the dose setting collar 30. As seen in FIG. 2, the forward movement is sufficient to move the rearward bung 18' towards the forward bung 18" to allow mixing of the therapeutic mixture. Thus initially the rearward bung 18' and the forward bung 18", with the diluent liquid between them, move forward together a sufficient distance for the forward bung 18" to uncover the bypass 20, whereupon the forward bung remains stationary, as the diluent liquid enters the forward chamber, until the rearward bung abuts the forward bung.

A spring 42 acting between the rearward end of the setting cylinder 32 and the flange 27 on the plunger 24 lightly biases the plunger to urge the threaded portion 24" on the plunger 24 into engagement with the corresponding female thread in the drive sleeve 34. The pushrod 38 may interface with the setting sleeve in a bayonet lock type arrangement (not shown) requiring the cap 40 to be rotated before it can be pushed into the shell 32, and also isolating the spring 42 and preventing the spring pushing the plunger onto the bung prior to use.

Following reconstitution, the device is made ready for injection by dialing in preset dose to prime the cartridge and to ensure that threads on the plunger and the drive collar are properly engaged. Thereafter the device may be used as a conventional pen injection device.

The relaxed length of the spring 42 is selected so that it ceases to apply pressure to the plunger 24 shortly after the threads on the plunger 24 and the drive sleeve 34 have engaged. If required a removable safety collar (not shown) may initially be releasably clipped around the exposed part of the pushrod 38 between the cap 40 and the dose setting collar 30, to prevent premature mixing of the substances in the chambers of the cartridge.

The invention claimed is:

1. An injection device configured for dispensing a substance from a dual or multi-chamber cartridge, said cartridge having a bung moveable in a first reconstitution phase of movement and a second, dosing phase of movement, said device comprising:
   a body portion (12);
   a plunger (24) mounted in said body portion for longitudinal movement with respect thereto in a forward dispensing direction to co-operate in use with said bung (18" 18');
   a plunger drive element (34) disposed adjacent said plunger for driving said plunger; and
   a drive mechanism releasable to apply drive to said plunger drive element;
   said plunger having a drive portion (24") adapted to drivingly engage a complementary drive portion (33a) on said drive element and adapted to impart dosing movement to said plunger (24);
   said drive portion extending only partly along said plunger to leave a forward non-drive portion;
   whereby, during a reconstitution phase, said plunger may be moved longitudinally forward from a position with the non-drive portion adjacent said drive element but not in driving engagement therewith, to bring its drive portion into driving engagement with the drive portion on said drive element.

2. The injection device according to claim 1, wherein said drive portions on said plunger drive element and said plunger are complementary threaded drive portions.

3. The injection device according to claim 2, wherein said plunger carries a male thread and said plunger drive element includes a bore having a female thread.

4. The injection device according to claim 3, wherein said non-drive portion of said plunger comprises a non-threaded portion sized to be moveable freely through said plunger drive element.

5. The injection device according to claim 4, including a mover element slideably moveable in said body portion and having an externally accessible push region for being pushed to engage said plunger and to move it to bring said complementary drive portions into driving engagement.

6. The injection device according to claim 4, including bias means for urging said plunger element towards complementary driving engagement with said plunger drive element.

7. The injection device according to claim 3, including a mover element slideably moveable in said body portion and having an externally accessible push region for being pushed to engage said plunger and to move it to bring said complementary drive portions into driving engagement.

8. The injection device according to claim 3, including bias means for urging said plunger element towards complementary driving engagement with said plunger drive element.

9. The injection device according to claim 2, including a mover element slideably moveable in said body portion and having an externally accessible push region for being pushed to engage said plunger and to move it to bring said complementary drive portions into driving engagement.

10. The injection device according to claim 2, including bias means for urging said plunger element towards complementary driving engagement with said plunger drive element.

11. The injection device according to claim 1, including a mover element slideably moveable in said body portion and having an externally accessible push region for being pushed to engage said plunger and to move it to bring said complementary drive portions into driving engagement.

12. The injection device according to claim 11, including means for releasably preventing longitudinal movement of said mover element.

13. The injection device according to claim 12, wherein said mover element includes a cap element defining said push region, said cap element being adapted to engage in snap engagement an end region of said injection device on completion of said reconstitution movement.

14. The injection device according to claim 11, wherein said mover element includes a cap element defining said push region, said cap element being adapted to engage in snap engagement an end region of said injection device on completion of said reconstitution movement.

15. The injection device according to claim 1, including bias means for urging said plunger element towards complementary driving engagement with said plunger drive element.

16. The injection device according to claim 15, wherein said bias means and said plunger are arranged such that said plunger is isolated from the influence of said bias means following driving engagement between said complementary drive portions.

17. The injection device according to claim 1, wherein the drive mechanism is arranged to apply a pre-selectable amount of angular movement to said plunger drive element on activation thereof.

18. The injection device according to claim 17, wherein said drive mechanism comprises:
   a user suitable dose setting member rotatably mounted on said body portion to set a dose;
   a spring acting between said dose setting means and said body portion, said spring being strained to a variable extent depending on movement of said dose setting member;
   a ratchet arrangement disposed between said dose setting member and said plunger drive element for allowing one way relative movement therebetween as said dose setting member is rotated to set a dose, and
   a trigger member operable to prevent rotary movement of said drive element and releasable to allow said spring to rotate said dose setting member and said plunger drive element by an amount corresponding to the set dose.

19. The injection device according to claim 18, wherein said dose setting element includes a generally cylindrical portion surrounding at least part of said plunger.

20. An injection device configured for dispensing a substance from a dual or multi-chamber cartridge, said cartridge having a bung moveable in a first reconstitution phase of movement and a second, dosing phase of movement, said device comprising:
- a body portion;
- a plunger mounted in said body portion for longitudinal movement with respect thereto in a forward dispensing direction to co-operate in use with said bung;
- a plunger drive element disposed adjacent said plunger for driving said plunger;
- a drive mechanism to apply a pre-selectable amount of angular movement to said plunger drive element on activation thereof;
- said plunger having a drive portion adapted to drivingly engage a complementary drive portion on said plunger drive element and adapted to impart dosing movement to said plunger;
- said drive portion extending only partly along said plunger to leave a forward non-drive portion;
- whereby, during a reconstitution phase, said plunger may be moved longitudinally forward from a position with the non-drive portion adjacent said drive element but not in driving engagement therewith, to bring its drive portion into driving engagement with the drive portion on said drive element.

* * * * *

UNITED STATES PATENT AND TRADEMARK OFFICE
CERTIFICATE OF CORRECTION

| | | |
|---|---|---|
| PATENT NO. | : 8,486,007 B2 | Page 1 of 1 |
| APPLICATION NO. | : 13/434340 | |
| DATED | : July 16, 2013 | |
| INVENTOR(S) | : Jeremy Marshall et al. | |

It is certified that error appears in the above-identified patent and that said Letters Patent is hereby corrected as shown below:

On the title page, please amend Item (22) to read as follows:

-- (22) PCT Filed: May 10, 2007 --

Signed and Sealed this
Thirty-first Day of December, 2013

Margaret A. Focarino
*Commissioner for Patents of the United States Patent and Trademark Office*